(12) United States Patent
Darnell

(10) Patent No.: US 7,226,435 B2
(45) Date of Patent: Jun. 5, 2007

(54) DRUG DELIVERY DEVICE

(75) Inventor: Lawrence W. Darnell, Cypress, TX (US)

(73) Assignee: Alcon, Inc., Hunenberg (CH)

( * ) Notice: Subject to any disclaimer, the term of this patent is extended or adjusted under 35 U.S.C. 154(b) by 45 days.

(21) Appl. No.: 11/194,723

(22) Filed: Aug. 1, 2005

(65) Prior Publication Data
US 2006/0084921 A1 Apr. 20, 2006

Related U.S. Application Data

(60) Provisional application No. 60/618,683, filed on Oct. 14, 2004.

(51) Int. Cl.
*A61M 5/00* (2006.01)
(52) U.S. Cl. .................................................. 604/207
(58) Field of Classification Search ............ 604/86–88, 604/133–135, 139, 164.02, 183, 184, 186, 604/201, 203, 206, 207, 214, 232, 233, 187
See application file for complete search history.

(56) References Cited

U.S. PATENT DOCUMENTS

| | | | |
|---|---|---|---|
| 4,227,528 A * | 10/1980 | Wardlaw | 604/139 |
| 4,316,463 A * | 2/1982 | Schmitz et al. | 604/135 |
| 4,781,688 A * | 11/1988 | Thoma et al. | 604/132 |
| 5,476,511 A | 12/1995 | Gwon | |
| 5,593,388 A * | 1/1997 | Phillips | 604/135 |
| 5,773,019 A | 6/1998 | Ashton | |
| 5,824,072 A | 10/1998 | Wong | |
| 5,951,516 A * | 9/1999 | Bunyan | 604/143 |
| 6,413,245 B1 | 7/2002 | Yaacobi | |
| 6,569,115 B1 * | 5/2003 | Barker et al. | 604/110 |
| 6,598,765 B2 * | 7/2003 | Pagel et al. | 222/214 |
| 6,811,548 B2 * | 11/2004 | Jeffrey | 604/207 |
| 2006/0047250 A1 * | 3/2006 | Hickingbotham et al. | 604/187 |

* cited by examiner

*Primary Examiner*—Kevin C. Sirmons
*Assistant Examiner*—Bhisma Mehta
(74) *Attorney, Agent, or Firm*—Jeffrey S. Schira

(57) ABSTRACT

A syringe-like device having a chamber in which a pressurizing piston reciprocates. The chamber is connected on one end to a vial containing a drug to be delivered to an eye and on the other end to a needle or cannula for administering the drug to an eye. Pulling proximally backwards on the piston creates a vacuum in the chamber and draws the drug out of the vial. Upon release of the piston, a spring pushes the piston forward, pressurizing the chamber. Delivery of the drug is controlled by a roller pinching off a section of compliant tubing between the chamber and the cannula, with a design similar to a peristaltic pump. A one-way valve prevents the drug from being expelled back into the vial. The flow rate of the drug out of the cannula can be controlled by rotation of the roller.

4 Claims, 2 Drawing Sheets

DRUG DELIVERY DEVICE

This application claims priority from Provisional U.S. patent application Ser. No. 60/618,683, filed Oct. 14, 2004.

BACKGROUND OF THE INVENTION

The present invention generally pertains to the delivery of ophthalmically acceptable pharmaceutically active agents to the back of the eye and more particularly to an apparatus for sub-Tenon delivery of a drug depot to the posterior segment of a human eye proximate the macula.

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, and glaucoma are several examples.

Age related macular degeneration (ARMD) is the leading cause of blindness in the elderly. ARMD attacks the center of vision and blurs it, making reading, driving, and other detailed tasks difficult or impossible. About 200,000 new cases of ARMD occur each year in the United States alone. Current estimates reveal that approximately forty percent of the population over age 75, and approximately twenty percent of the population over age 60, suffer from some degree of macular degeneration. "Wet" ARMD is the type of ARMD that most often causes blindness. In wet ARMD, newly formed choroidal blood vessels (choroidal neovascularization (CNV)) leak fluid and cause progressive damage to the retina.

In the particular case of CNV in ARMD, two main methods of treatment are currently being developed, (a) photocoagulation and (b) the use of angiogenesis inhibitors. However, photocoagulation can be harmful to the retina and is impractical when the CNV is in proximity of the fovea. Furthermore, photocoagulation often results in recurrent CNV over time. Oral administration of anti-angiogenic compounds is also being tested as a systemic treatment for ARMD. However, due to drug-specific metabolic restrictions, systemic administration usually provides sub-therapeutic drug levels to the eye. Therefore, to achieve effective intraocular drug concentrations, either an unacceptably high dose or repetitive conventional doses are required. Various implants have also been developed for delivery of anti-angiogenic compounds locally to the eye. Examples of such implants are disclosed in U.S. Pat. No. 5,824,072 to Wong, U.S. Pat. No. 5,476,511 to Gwon et al., and U.S. Pat. No. 5,773,019 to Ashton et al.

In addition, it is known to use a straight, ⅝ inch long, 25 gauge needle to perform sub-Tenon injection of corticosteroids for the treatment of posterior uveitis or macular edema associated with uveitis or anterior segment surgery. In such methods, a physician attempts to dispose the tip of the needle near the macula but without penetrating the posterior ciliary arteries or the optic nerve. However, because the physician cannot see the tip, as well as movement of the eyeball within the orbit due to contact with the straight needle, it is very difficult to precisely place the tip at the desired location near the macula. For the same reasons, it is also very difficult to determine whether the tip is correctly positioned below the Tenon's capsule. Such methods do not insure a consistent delivery of a specific quantity of drug to a region over the macula. In fact, the literature reports that only about 57 percent of injections using this method result in drug being placed in the sub-Tenon space overlying the macular area. In addition, moving a straight needle along the curved surface of the sclera causes "tenting" or stretching of the overlying Tenon's capsule. Such movement may cause penetration of the Tenon's capsule, allowing drug to be injected into surrounding tissues. Furthermore, such movement may also cause inadvertent penetration of the sclera, resulting in injection of drug into the vitreous cavity. More importantly, penetration of the sclera may result in significant damage to the eye or even a loss of sight. Documented complications of such penetrations include orbital hemorrhage, central retinal vein occlusion, and central retinal artery occlusion.

A further concern with sub-Tenon delivery of a drug depot to the posterior segment of a human eye proximate the macula is that the drug must be administered slowly and under relatively low pressure so as to be retained in the tissue rather than leaking back out of the tissue through the needle channel.

Therefore, a need exists in the field of ophthalmology for an improved apparatus for sub-Tenon delivery of a drug depot to the posterior segment of a human eye proximate the macula.

BRIEF SUMMARY OF THE INVENTION

The present invention improves upon the prior art by providing a syringe-like device having a chamber in which a pressurizing piston reciprocates. The chamber is connected on one end to a vial containing a drug to be delivered to an eye and on the other end to a needle or cannula for administering the drug to an eye. Pulling proximally backwards on the piston creates a vacuum in the chamber and draws the drug out of the vial. Upon release of the piston, a spring pushes the piston forward, pressurizing the chamber. Delivery of the drug is controlled by a roller pinching off a section of compliant tubing between the chamber and the cannula, with a design similar to a peristaltic pump. A one-way valve prevents the drug from being expelled back into the vial. The flow rate of the drug out of the cannula can be controlled by rotation of the roller.

Accordingly, one objective of the present invention is to provide a syringe-like device having a chamber in which a pressurizing piston reciprocates.

Another objective of the present invention is to provide a device for the sub-Tenon delivery of a drug depot to the posterior segment of a human eye proximate the macula.

Yet another objective of the present invention is to provide a drug delivery device wherein the flow rate of the drug being delivered can be controlled.

These and other advantages and objectives of the present invention will become apparent from the detailed description and claims that follow.

DETAILED DESCRIPTION OF THE INVENTION

Figure 1:
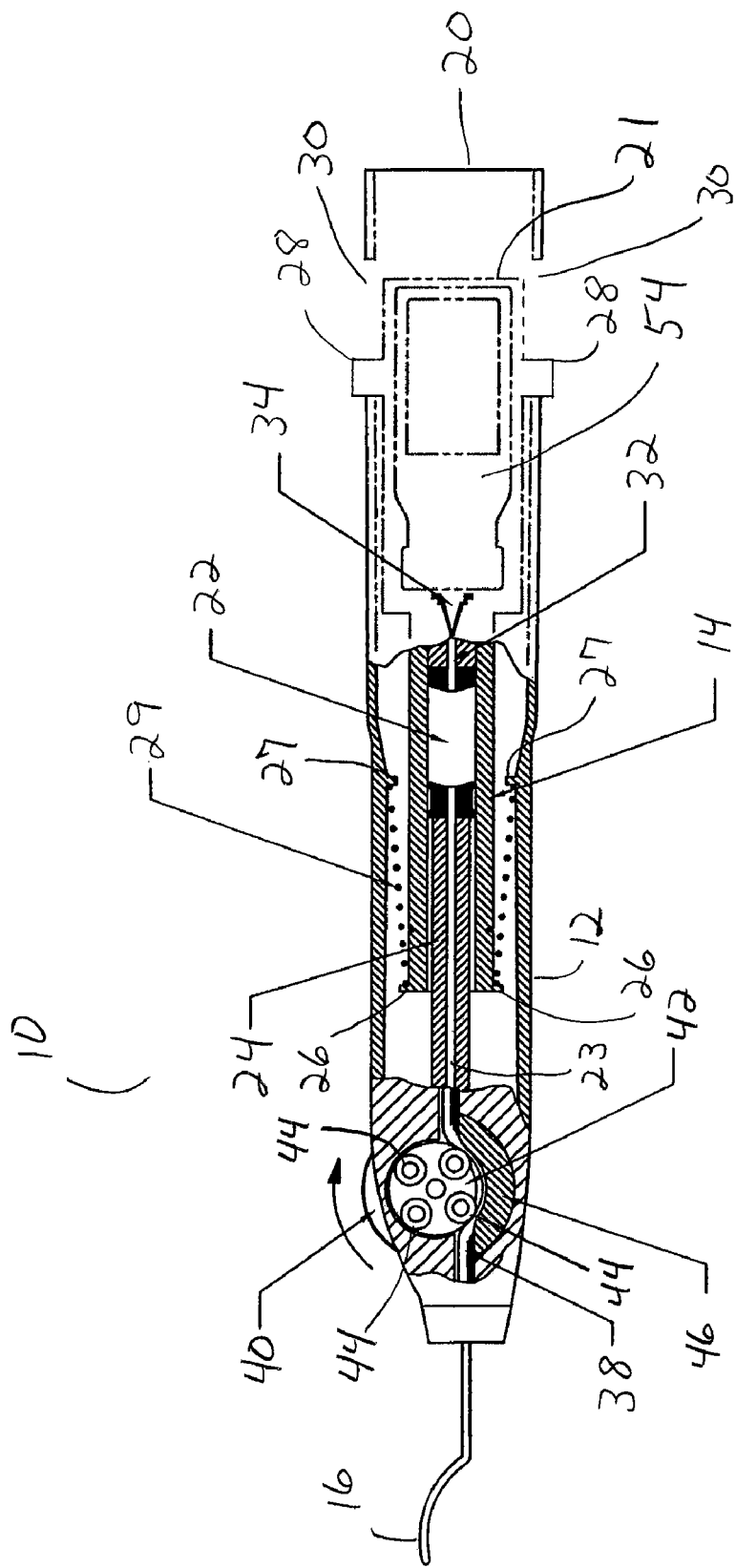
FIG. 1 is an enlarged, partial cross-sectional view of the drug deliver device of the present invention.
Figure 2:
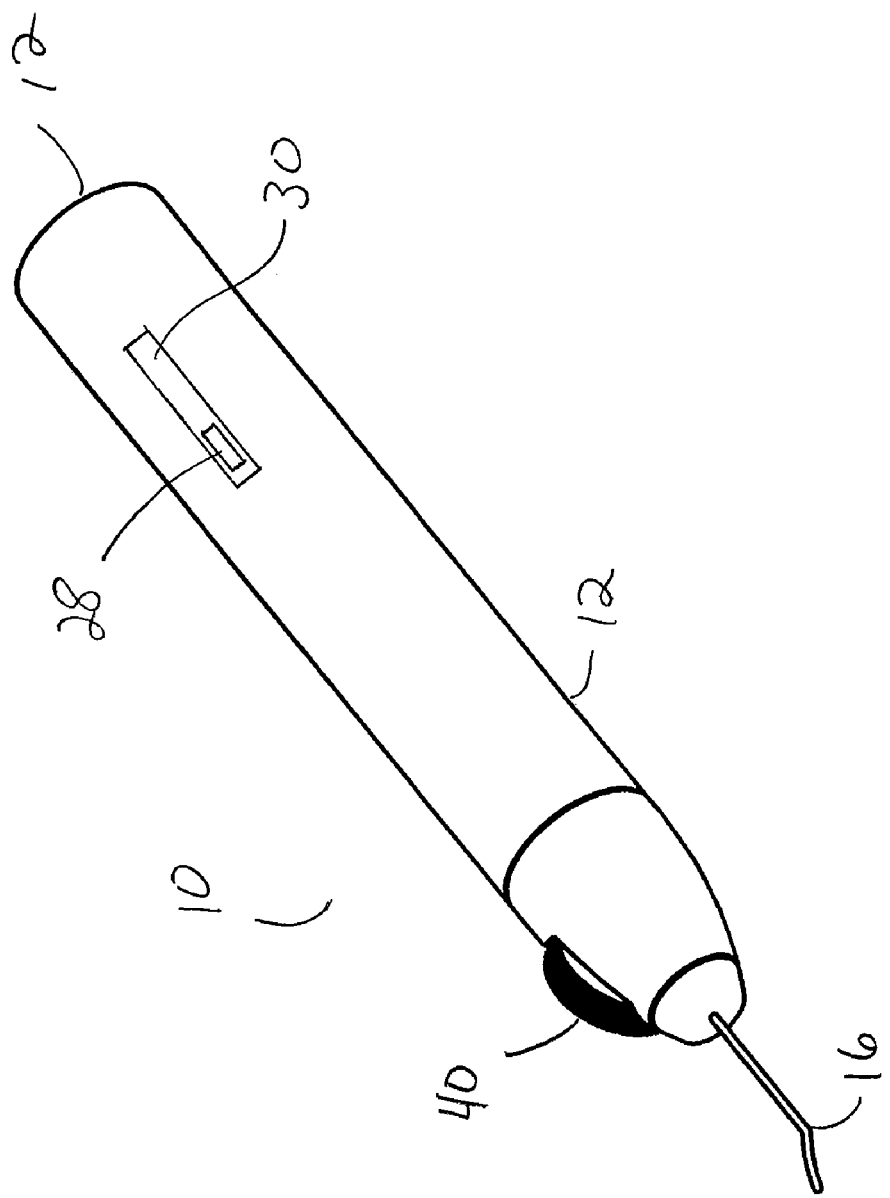
FIG. 2 is an enlarged prospective view of the drug deliver device of the present invention.

As best seen in FIGS. 1-2, drug delivery device 10 of the present invention generally comprises body 12, cylinder 14 and cannula 16. Cannula 16 may be any suitable cannula, such as the cannula described in U.S. Pat. No. 6,413,245 B1 (Yaacobi, et al.). Body 12 is generally hollow and proximal end 20 of body 12 is generally open and sized to reciprocally receive cylinder 14. Cylinder 14 likewise is open at proximal end 21 and is sized to receive sealed vial 54 of a drug to be delivered. Located on cylinder 14 opposite proximal end 21 is hollow interior chamber 22. Piston 24 is fixed to body 12 and is generally sized to reciprocate snugly within chamber 22 and contains lumen 23 that communicates with chamber 22. Lumen communicates with cannula 16 through compliant tubing 38, thereby providing a continuous fluid path between chamber 22 and cannula 16. Cylinder 14 contains flange 26 that cooperates with flange 27 within body 12 to retain compression spring 29. Cylinder 14 contains a plurality of finger tabs 28 that fit within slots 30 in body 12 and allow finger tabs 28 to be grasped when cylinder 14 is installed within device 10. Pulling on finger tabs 28 forces spring 29 to compress between flanges 26 and 27. Such movement pulls cylinder 14 away from piston 24 and creates a vacuum within chamber 22, thereby drawing fluid out of vial 54 through vial aspiration spike tube 32. Release of tabs 28 causes spring 29 to expand, pushing cylinder 14 over piston 24 and pressurized chamber 22. Flow is prevented from chamber 22 back into vial 54 by check valve 34. The pressurized fluid contained with chamber 22 is forced out lumen 23, through tubing 38 and into cannula 16. Flow through tubing 38 is prevented by actuator dial 40 that is connected to roller head 42. Roller head 42 contains a plurality of rollers 44 that pinch tubing 38 against stator 46. Actuator dial 40 can be rotated in only one direction so as not to force fluid back into lumen 23.

In use, sealed vial 54 containing a drug to be delivered is placed in open proximal end 21 of cylinder 14 so that spike tube 32 pierces into vial 54. Cylinder 14 is drawn back against spring 29 by grasping and pulling on finger tabs 28. As cylinder 14 is drawn back, chamber 22 enlarges, thereby creating a vacuum in chamber 22. The created vacuum draws the drug out of vial 54 through spike tube 32 and into chamber 22. Once the drug is drawn out of vial 54 and into chamber 22, cylinder 14 is released, allowing spring 29 to expand, pushing cylinder 14 over piston 24, thereby creating pressure within chamber 22. Fluid flows from chamber 22 into lumen 23 and tubing 38 but is periodically prevented from entering cannula 16 because tubing 38 is pinched shut by rollers 44. Rotation of actuator dial 40 episodically pinches and unpinches tubing 38, allowing a small amount of fluid (on the order of 0.01 cc's and 0.1 cc's) periodically to flow into cannula 16 and to the operative site.

One skilled in the art will recognize that by varying the size of chamber 22, piston 24 tubing 38 and roller head 42, as well as varying spring 29, different fluid pressures and flow rates can be achieved.

I claim:

1. A drug delivery device, comprising:
    a) a generally hollow, open body;
    b) a cylinder containing a chamber and reciprocating over a piston, the cylinder located within the body and sized and shaped to receive a vial of a drug to be delivered;
    c) a cannula generally located on the body opposite the vial, the cannula fluidly connected to the chamber through a tubing;
    d) a roller head located on the body, the roller head connected to an actuator dial and containing a plurality of rollers, rotation of the actuator dial causing periodic pinching and unpinching of the tubing; and
    e) a spring against which the cylinder reciprocates, the spring forcing the cylinder over the piston.

2. The drug delivery device of claim 1 wherein the piston contains a lumen that provides a fluid path between the chamber and the tubing.

3. The drug delivery device of claim 2 wherein reciprocation of the cylinder over the piston causes fluid in the chamber to be forced down the lumen.

4. The drug delivery device of claim 1 wherein reciprocation of the cylinder over the piston draws a fluid from the vial and into the chamber.

\* \* \* \* \*